United States Patent [19]

Caillod et al.

[11] Patent Number: 5,225,389

[45] Date of Patent: Jul. 6, 1993

[54] CATALYSTS FOR THE GASEOUS PHASE OXIDATION OF OLEFINS INTO α,β-UNSATURATED ALDEHYDES

[75] Inventors: Jack Caillod, Taverny; Philippe Jaeger, Salindres; Olivier Legendre, Herblay, all of France

[73] Assignee: Rhone-Poulenc Chimie, Courbevoie, France

[21] Appl. No.: 811,128

[22] Filed: Dec. 20, 1991

[30] Foreign Application Priority Data

Dec. 20, 1990 [FR] France .................. 90 16388

[51] Int. Cl.$^5$ .................. B01J 27/185; B01J 27/188; B01J 27/192
[52] U.S. Cl. .................. 502/205; 502/212; 568/480
[58] Field of Search .................. 502/205, 212; 568/480

[56] References Cited

U.S. PATENT DOCUMENTS

| | | | |
|---|---|---|---|
| 4,040,978 | 8/1977 | Li | 252/437 |
| 4,168,246 | 9/1979 | Li | 252/437 |
| 4,276,196 | 6/1981 | Dalton et al. | 252/435 |
| 4,298,763 | 11/1981 | Engelbach et al. | 568/480 X |
| 4,332,971 | 6/1982 | Dalton et al. | 568/480 |
| 4,382,880 | 5/1983 | Derrien | 252/465 |
| 4,438,217 | 3/1984 | Takata et al. | 502/212 X |
| 4,521,618 | 6/1985 | Arntz et al. | 562/535 |
| 4,539,409 | 9/1985 | Arntz et al. | 546/286 |
| 4,621,072 | 11/1986 | Arntz et al. | 502/504 |
| 5,082,819 | 1/1992 | Boeck et al. | 502/212 |

Primary Examiner—W. J. Shine
Attorney, Agent, or Firm—Burns, Doane, Swecker & Mathis

[57] ABSTRACT

Catalyst compositions well adopted for the oxidation of olefins into α,β-unsaturated aldehydes, e.g., for the oxidation of propylene into acrolein, comprise a particulate support substrate uniformly coated with 15% to 33% by weight of an adherent layer of a catalytically active phase, such support substrate comprising inert and solid spheres having a diameter ranging from 0.5 to 6 mm, such catalytically active phase comprising a catalytically effective amount of bismuth and iron molybdate, dopant amounts of phosphorus and potassium and, optionally, at least one other catalytically active metal or non-metal, and the phosphorus and the potassium each being present in such catalytically active phase in an atomic quantity ranging from 0.005 to 0.06 per 12 atoms of molybdenum, or of molybdenum plus any tungsten therein.

10 Claims, No Drawings

CATALYSTS FOR THE GASEOUS PHASE OXIDATION OF OLEFINS INTO α,β-UNSATURATED ALDEHYDES

CROSS-REFERENCE TO COMPANION APPLICATION

Copending application Ser. No. 07/811,127, filed concurrently herewith and assigned to the assignee hereof.

BACKGROUND OF THE INVENTION

1. Field of the Invention

The present invention relates to novel catalytic compositions for the preparation of α,β-unsaturated aldehydes by oxidation of olefins in the gaseous phase.

This invention especially relates to catalytic compositions comprising a support substrate (or central core) in the form of inert solid spheres having an adherent layer of a catalytically active phase of the bismuth and iron molybdate type coated thereon, doped with potassium and phosphorus and, if necessary, with one or more other metallic or non-metallic elements.

2. Description of the Prior Art

French Patent No. 2,047,199 describes oxidation catalysts corresponding to the general formula:

$$Ni_aCo_bFe_cBi_dL_eM_hMo_fO_g$$

in which L is particularly phosphorus, M is particularly potassium, a and b are numbers ranging from 0 to 15 with the sum (a+b) ranging from 2 to 15, c is a number ranging from 0.5 to 7, d is a number ranging from 0.to 4, e is a number ranging from 0 to 4, f has a value of 12, g is a number ranging from 35 to 85, and h is a number ranging from 0.01 to 0.5.

These catalysts are prepared by formulating a suspension in aqueous medium from various precursors of the elementary constituents of the catalysts, by adding a support (such as a silica gel) to said suspension which is essentially a paste, and by heating this to dryness to provide a cake which is then treated at elevated temperature in the presence of air and oxygen.

The catalysts are employed in the form of particles or of tablets.

These catalysts, both in bulk form and diluted, are effective, but they present difficulties over the course of an oxidation process on an industrial scale. Indeed, in a fixed bed, locally elevated temperatures may arise to initiate an undesirable violence of the reaction.

French Patent No. 2,202,729 describes that it is advantageous to employ catalysts for the oxidation of propylene to acrolein which are prepared by coating, namely, formed of a catalytically active layer of the same composition, but deposited onto the external surface of an inert support of at least 20 microns in diameter, instead of diluting it with a support introduced with the metallic salts. It is then possible to better control the evolution of the heat of reaction in fixed bed processes.

Nevertheless, this particular technique for producing the catalyst requires a significant portion thereof to be constituted by the inert support (66% by weight of the finished catalyst, according to the sole example of this '729 patent). The fraction reserved for the active phase in comparison with the former simply diluted catalysts is decreased, which results in a very disadvantageous decrease in the activity of the catalysts.

This may manifest itself industrially in the obligation either to use larger reactors to preserve the production capacity and identical operating conditions, or to increase the reaction temperature to preserve the production capacity and the size of the reactor. In the first instance, the major disadvantage is economic. In the second instance, two disadvantages are presented: the selectivity for acrolein will diminish and the activity of the catalyst will decrease more rapidly over the course of time.

U.S. Pat. No. 4,298,763 describes, for the oxidation of propylene into acrolein, a calcined catalytic composition (active phase) corresponding to the general formula:

$$Mo_{12}Bi_{0.1-4}Fe_{0.5-6}M2_bM3_cM4_dM5_eO_x$$

in which M2 is nickel and/or cobalt, b is a number ranging from 2 to 12, M3 is particularly K, c is a number ranging from 0.01 to 0.1 and preferably from 0.03 to 0.09, M4 is P, d is a number ranging from 0 to 1 and preferably from 0.01 to 0.2, M5 is In and/or Na, e is a number ranging from 0 to 0.5 and preferably from 0.01 to 0.2, and x is the number of atoms of oxygen required to satisfy the valencies of the other constituents.

This active phase is deposited as a layer of thickness 150 to 1500 μm onto a support which is also a central core of diameter greater than 100 μm and of surface area less than 15 m²/g.

The deposition of the layer of calcined and pulverulent catalytic material, the dimension of the particles ranging from 0.1 to 300 μm, is carried out in moist medium, the support particles being vigorously stirred and controlled operating conditions moreover being required.

The layer coating the central supporting core constitutes at least 50% of the weight of the support, namely, at least 33% by weight of the finished catalyst and at most 250% of the weight of the support, namely, at most 71.4% by weight of the finished catalyst.

Prior to being used for the oxidation of olefins, the coated catalyst is dried and, if necessary, calcined at a temperature of 400° to 700° C.

Even if these catalysts exhibit a satisfactory catalytic activity, the very complex process for the preparation thereof militates against its reproducibility and against assuring a constant quality of the catalysts thus prepared. In addition, it is well known to this art that, when the thickness of the coating layer increases such that it constitutes on the order of 20% by weight of the catalyst, the mechanical properties of said layer are insufficient for use of the catalysts on an industrial scale in fixed bed reactors (cf., for example, U.S. Pat. No. 4,521,618).

SUMMARY OF THE INVENTION

Accordingly, a major object of the present invention is the provision of improved catalysts by coating a catalytically active phase of the bismuth and iron molybdate type, doped with potassium and phosphorus, onto a particulate support substrate, said improved catalysts exhibiting both a long-lived and high catalytic activity and selectivity, on an industrial scale in fixed bed reactors, for the preparation of α,β-unsaturated aldehydes by oxidation of olefins in the gaseous phase and, in particular, for the preparation of acrolein by oxidation of propylene.

Briefly, the present invention features a catalytic composition comprising:

(i) a particulate support substrate in the form of inert solid spheres having a diameter ranging from 0.5 to 6 mm, and (ii) a catalytically active phase based on bismuth and iron molybdate, doped with potassium and phosphorus and, if appropriate, with one or more other metallic or non-metallic elements, said support substrate being uniformly coated with an adherent layer of said catalytically active phase and wherein:

(a) the phosphorus and the potassium are each present in an atomic quantity ranging from 0.005 to 0.06 per 12 atoms of molybdenum or of molybdenum and tungsten in said phase and (b) said catalytically active phase constitutes from 15% to 33% by weight of the catalytic composition.

The present invention also features a process for the oxidation of olefins in the gaseous phase employing such a catalytic composition and, in particular, a process for the oxidation of propylene into acrolein.

DETAILED DESCRIPTION OF THE PREFERRED EMBODIMENTS OF THE INVENTION

More particularly according to the present invention, the catalytic composition comprises a support in the form of inert solid spheres having a diameter ranging from 0.5 to 6 mm. The precise value of the diameter of the spheres can be determined by one skilled in this art as a function of the loss of charge introduced in the reactor. The nature of the support is not critical since it is chemically inert with respect to the reagents under the reaction conditions selected. Exemplary supports which are suitable for the preparation of the compositions according to the invention include silica, alumina, silica-alumina, sintered clay, carborundum, magnesia and magnesium silicate. If it is important that the support have a surface roughness to provide a mechanical resistance sufficient for use in a fixed bed for a duration acceptable on an industrial scale, the surface roughness, defined by the height of the unevennesses (or protuberances) relative to the mean diameter of the spheres, can vary over wide limits. Preferably, the roughness thus defined ranges from 0.1 to 0.2

The catalytic composition according to the present invention also comprises a catalytically active phase based on bismuth and iron molybdate, doped with potassium and phosphorus and, if appropriate, by one or more other metallic or non-metallic elements.

This type of catalytically active phase is well known to this art and is easily prepared by such means as the mixing of suitable salts of the elementary constituents in water, followed by evaporation to dryness, as described in French Patents Nos. 1,514,167 and 2,364,061; or by atomization of a suspension obtained after mixing suitable salts as described in U.S. Pat. No. 4,298,763 and European Patent Applications EP-A-25,715 and EP-A-77,675.

According to an essential characteristic of the composition according to the invention, the phosphorus and the potassium are each present in an atomic quantity ranging from 0.005 to 0.06 per 12 atoms of molybdenum or of molybdenum and tungsten in said catalytically active phase.

Indeed, it has now unexpectedly been determined that better catalytic activities are provided when lesser amounts of the dopants, phosphorus and potassium, are retained. Preferably, the content of each of these will range from 0.01 to 0.03. To attain as high as possible a catalytic activity, it is advantageous to maintain the atomic ratio P/K from 0.3 to 3, inclusive, and, preferably, from 0.5 to 1.5, inclusive.

According to another essential characteristic of the composition according to the invention, the catalytically active phase constitutes from 15% to 33% by weight of the total composition and, preferably, from 20% to 30% by weight. Below 15% by weight, the activity of the catalyst would be insufficient on an industrial scale and above 33% by weight, the mechanical resistance of the catalyst would be too uncertain for prolonged industrial use.

In a particularly preferred embodiment of the invention, the composition comprises a catalytically active phase corresponding to the general formula:

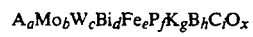

$$A_a Mo_b W_c Bi_d Fe_e P_f K_g B_h C_i O_x$$

in which A is an atom of cobalt, nickel, manganese, magnesium and/or lead, and preferably of cobalt and/or of nickel; B is an atom of arsenic and/or of boron; C is an atom of an alkali metal other than potassium and/or an atom of an alkaline earth metal other than magnesium; a is the sum of the numbers of the atoms of the elements A and ranges from 2 to 12, inclusive (when A is cobalt alone, a ranges from 8 to 10, inclusive); b is a number ranging from 10 to 12, inclusive; c is a number ranging from 0 to 2, inclusive, and the sum (b+c) has a value of 12; d is a number ranging from 0.5 to 4, inclusive; e is a number ranging from 0.5 to 4, inclusive; f and g are each numbers ranging from 0.005 to 0.06, inclusive, and, preferably, from 0.01 to 0.03, inclusive; h is the sum of the numbers of atoms of the elements B and ranges from 0 to 4, inclusive; i is the sum of the numbers of atoms of the elements C and ranges from 0 to 0.5, inclusive; and x is the number of atoms of oxygen required to satisfy the valencies of the other constituents.

Preferably, A is an atom of cobalt. As indicated above, f/g advantageously ranges from 0.3 to 3, inclusive, and preferably from 0.5 to 1.5, inclusive.

While not wishing to be bound by or to any particular theory, it is reasoned that a portion of the good activity of the catalysts according to the invention can be attributed to the presence in the coating layer of a specific crystallographic phase designated "phase X", corresponding to the stoichiometry $BiFe_1Mo_2O_{12}$ and the detection of which can be accomplished by subjecting a powder, obtained by attrition of the finished catalytic composition, to examination by X-ray diffraction.

Such x-ray diffraction spectrum is the following:

| d (A) | Relative visual intensity |
| --- | --- |
| 3.17 | very large |
| 3.14 | very strong |
| 2.91 | strong |
| 2.69 | weak |
| 2.63 | strong |
| 1.87 | very very weak |

The preparation of the compositions according to the invention can be carried out by a variety of techniques and, in particular, by first preparing a catalytically active phase by any known technique, such as the mixing of suitable salts of the elementary constituents in water followed by evaporation to dryness.

The suitable salts typically employed are soluble in water and contain anions and cations which can be decomposed by heat during the subsequent processing. These include, for example, ammonium heptamolybdate and ammonium paratungstate for molybdnum and tungsten, and the nitrates of cobalt, iron, nickel and bismuth for the metals. The dopants are also introduced in the form of soluble and decomposable compounds, for example 85% phosphoric acid, arsine, soda, potash, magnesia or the alkali metal or alkaline earth metal acetates, nitrates or phosphates.

Once the mixing of the salts has been carried out, a precursor can be produced by evaporation. The water of the resulting suspension is evaporated by heating to from 60° to 90° C. with stirring for the time necessary to obtain a non-fluid paste. The stirring and the heating are then terminated. The paste thus obtained, spread to a thickness of about 2 cm, is dried in air at 120° C. for 16 hours. The precursor thus obtained may be calcined after having been cut into 1 to 2 cm pieces. The calcination is carried out by progressively increasing the temperature 100° to 200° C. per hour, because of the risks associated with the exothermic decomposition of ammonium nitrate at 230° C. The temperature is then maintained at a stable value from 400° to 460° C. for 6 hours and cooling is next carried out over the course of a few hours. The active catalytic phase thus prepared is then ground in order that its particle size does not exceed 400 micrometers.

The precursor can also be prepared according to a variant comprising precipitation with the addition of ammonia upon completion of mixing of the salts to increase the pH to about 7, as described in French Patent No. 2,481,146. The ammonia solution contains from 50 to about 250 g of ammonia and is added at a rate of from about 20 to about 200 g of ammonia per hour and per liter of mixture. It is preferable to then heat the suspension to from 20° to 100° C. for about one hour to complete the precipitation of the species. The suspension is then filtered. The filter cake is then spread in a thickness of less than 2 cm and calcined as described above in respect of the technique for evaporation, to provide the active phase. In this embodiment, dopants based on soluble salts of phosphorus and of potassium are not introduced into the suspension of metallic salts, but are subsequently introduced by impregnation of the "intermediate" active phase or of the "intermediate" catalyst, or during the coating.

The final catalysts are produced by coating ground, intermediate or finished, active phases. This conventional method entails depositing a layer of intermediate or finished active phase onto inert but rough spheres. Various coating procedures are described in the patents noted above. The preferred embodiment includes carrying out the coating in a cylindrical coater in which 80 to 160 kg of inert and rough spheres from which the dust has carefully been removed are revolved. These spheres are advantageously comprised of clay sintered at high temperature, but it is possible to use any other inert and rough support, as indicated above, 30 to 50 kg of active phase and 8 to 15 liters of aqueous solution of an adhesive agent and, optionally, other additives are then introduced into the coater. In a preferred embodiment, the introduction of the active phase in powder form is carried out simultaneously with the spraying of the aqueous solution onto the previously moistened spheres. Once the spheres have been covered with the entire active phase, they are dried by hot air, at a temperature of 80° to 150° C., for 2 to 30 minutes, then introduced into ovens. The temperature of these ovens is increased linearly over the course of 3 to 15 hours to a stable value of from 450° to 500° C. Cooling is then carried out over the course of 3 to 10 hours. In another preferred embodiment, a second calcination is carried out successively and under the same conditions of variation of temperature as the first calcination.

The present invention also features a process for the oxidation of olefins in the gaseous phase employing such a catalytic composition and, more particularly, a process for the oxidation of propylene into acrolein.

In general, the oxidation process is conducted by fixed bed technique in a multitubular reactor. In one embodiment, each tube has an interior diameter of 15 to 30 mm and a length of 2 to 5 meters, preferably of 3 to 4 meters, and is surrounded by a bath of heatdissipating fluid permitting the removal of the calories liberated by the reaction, for example a eutectic mixture of fused salts. The reagents are introduced into the reactor in gaseous state at a temperature of from 100° to 250° C. For the oxidation of propylene, they are, in general, constituted of 6% to 10 mol % of propylene, 50% to 65 mol % of air and 25% to 40 mol % of water vapor. It is possible to replace all or a portion of the water vapor by inert gases recycled upon completion of the operation. These inert gases contain nitrogen, water vapor and carbon oxides. The pressure of the reagents at the inlet to the reactor ranges from 1 to 3 bars, preferably slightly higher than atmospheric pressure to take into account losses of charge in the reactor and in the remainder of the apparatus. In actual practice, this pressure advantageously ranges from 1.5 to 2.5 bars.

For the oxidation of propylene, the temperature of the salt bath advantageously ranges from 280° to 360° C.

In order to further illustrate the present invention and the advantages thereof, the following specific examples are given, it being understood that same are intended only as illustrative and in nowise limitative.

EXAMPLE 1

Preparation of a catalytic composition according to the invention (a) Preparation of the Precursor of the Active Phase The precursor was obtained by reaction between a solution (A) of nitrates of Co, Fe, Bi and K and a solution (B) of ammonium heptamolybdate containing phosphoric acid.

The solution (A) of nitrates of Co, Fe, Bi and K, the pH of which was less than 1, was obtained by mixing 4 solutions prepared separately, as follows:

(i) 116.4 g of hydrated cobalt nitrate of the formula $Co(NO_3)_2 \cdot 6H_2O$ were dissolved at ambient temperature in 50 ml of deionized water; the pH of the solution thus obtained was 1.8;

(ii) 16.2 g of hydrated ferric nitrate the formula $Fe(NO_3)_2 \cdot 9H_2O$ were dissolved at ambient temperature in 12.5 ml of deionized water; the pH of the solution thus obtained was 0.7;

(iii) 2 ml of concentrated nitric acid of density 1.4 g/l were added to 14 ml of deionized water, then 19.4 g of hydrated bismuth nitrate of formula $Bi(NO_3)_3 \cdot 5H_2O$ were added at ambient temperature; the pH of the solution thus obtained was 0;

(iv) 0.20 g of potassium nitrate of formula $KNO_3$ was dissolved at ambient temperature in 2.5 ml of deionized water.

The solution of ammonium heptamolybdate containing phosphoric acid was obtained by dissolving 84.75 g of ammonium heptamolybdate at ambient temperature in 380 ml of deionized water to which was added 0.227 g of 85% phosphoric acid in 2 ml of water. The pH of this solution (B) was 5.3.

To obtain the precursor of the active phase, the solution (A) of the nitrates was added slowly (over the course of 20 minutes) to the solution (B) of heptamolybdate, with stirring. During this addition, stirring was ensured by a stirrer provided with helical blades revolving at 1,100 revolutions per minute.

Upon completion of the addition, a suspension of salmon-pink color was produced which was maintained stirred for half an hour at ambient temperature. During this stirring, the pH became stable at 1.1.

The mixture was heated with stirring to 80° C. to evaporate the water; at the end of two hours, a non-fluid paste was obtained. The stirring and heating were terminated. The paste thus obtained, spread to a thickness of about 2 cm, was dried in air at 120° C. for 48 hours. A solid was then obtained which was the precursor of the active phase.

(b) Preparation and Processing of the Active Phase

The solid thus obtained was cut into pieces of about 1 cm and placed in the calcination oven in a thickness of 2 to 3 cm. Precalcination was carried out at 400° C. for 6 hours. The increase in temperature of the oven was not too rapid because of the exothermic decomposition reaction of ammonium nitrate at 230° C. The rate of increase of temperature was on the order of 250° C. per hour.

The solid thus obtained was the active phase whose composition was $Co_{10}Mo_{12}Fe_1Bi_1K_{0.05}P_{0.05}O_x$; it was ground to provide a particle size of less than 400 micrometers.

(c) Coating of the Support with the Active Phase 52 g of ground active phase were added to a solution of 8 g of glucose in 70 ml of deionized water at ambient temperature. The entire mass was heated at 70° C. with good stirring for about 30 min.

The above suspension was poured into a coater of 20 cm diameter containing 210 g of clay spheres sintered at 1,100° C., having a surface roughness of 0.3 and diameter 4.8 mm and heated to 70° C. The rotation of the coater was maintained and the temperature was maintained at 80° C. until all the water had completely evaporated. The spheres thus produced were then dried at 140° C. for 2 hours. They were then placed in a calcination oven in a thickness of 2 to 3 cm and then calcined at 480° C. for 6 h under a confined atmosphere. This first calcination eliminated the glucose. It was followed by slow cooling and then by a second calcination at 480° C., also for 6 hours. 259.5 g of final catalyst in which the amount of weight of active phase was 19.1% was thus produced.

EXAMPLE 2

Preparation of a First Control Catalytic Composition

The procedure of Example 1 was repeated with the exception that 0.285 g of phosphorus pentoxide was introduced into the solution already containing ammonium heptamolybdate and 0.4 g of potassium nitrate into the solution containing the metallic nitrates.

The chemical composition of the active phase prepared in this manner was therefore $Co_{10}Mo_{12}Fe_1Bi_1K_{0.1}P_{0.1}O_x$ and was not according to the present invention.

The sequence of operations was identical to that of Example 1. The amount by weight of active phase in the finished catalyst was 19.1%.

EXAMPLE 3

Preparation of a Second Control Catalytic Composition

The procedure of Example 1 was repeated, except that 1.4 g of phosphorus pentoxide was introduced into the solution already containing ammonium heptamolybdate and 2.0 g of potassium nitrate into the solution containing the metallic nitrates.

The chemical composition of the active phase thus prepared was therefore $Co_{10}Mo_{12}Fe_1Bi_1K_{0.5}P_{0.5}O_x$ and was not within the ambit of the present invention.

The sequence of operations was identical to that of Example 1. The amount by weight of active phase in the finished catalyst was 18.7%.

EXAMPLE 4

Determination of the Catalytic Activity of the Various Compositions

The catalysts thus prepared were tested in the controlled oxidation of propylene to acrolein in a reactor of internal diameter 21 mm and 50 cm height, containing 100 ml of catalyst.

The reaction mixture introduced into the reactor heated by a sand bath contained in percent by volume: 7% of propylene, 57% of air and 36% of water vapor. The supply of propylene was adjusted to provide a charge of approximately 166 g of propylene per hour and per liter of catalyst. The pressure at the outlet of the reactor was adjusted to 1.8 bar absolute.

The effluents from the reactor comprised a gaseous mixture of nitrogen, oxygen, water vapor, propylene, acrolein, acrylic acid, acetic acid, acetaldehyde, carbon monoxide and dioxide, and other impurities in minor amounts. Gas phase chromatographs permitted the proportions of each of these products to be determined and, therefore, the catalytic performances to be calculated, namely, The rate of conversion, designated $X_g$ $$X_g = \frac{\text{Number of moles of product } i \text{ formed}}{\text{Number of moles of propylene initially}} \times 100$$

The selectivity for product $i$, designated $S_i$ $$S_i = \frac{\text{Number of moles of product } i \text{ formed}}{\text{Number of moles of propylene converted}} \times 100$$

and $R_i$ which is the yield of product i. The yield is the product of the conversion $x_g$ multiplied by the selectivity for product i: $R_i = X_g \times S_i$ The results obtained using the catalysts of Examples 1 to 3 are reported in Table I below:

TABLE I

| Example | Dopants | Amount by weight (%) | Temperature of bath °C. | $X_g$ (%) | $S_{acrolein}$ (%) | $S_{acrylic}$ (%) | $S_{CO-CO_2}$ (%) | $R_{acrolein}$ (%) |
|---|---|---|---|---|---|---|---|---|
| 1 | $K_{0.5}P_{0.05}$ | 19.1 | 351 | 92.2 | 82.5 | 7.6 | 3.7 | 76.0 |
| 2 | $K_{0.1}P_{0.1}$ | 19.1 | 360 | 87.3 | 85.5 | 6.5 | 2.0 | 74.6 |
| 3 | $K_{0.5}P_{0.5}$ | 18.7 | 349 | 43.8 | 89.9 | 2.1 | 0.9 | 39.4 |

It will be seen that the increase in the content of the dopants, phosphorus and potassium, added in the same atomic quantity, decreased the activity of these catalysts, all other conditions being equal.

Either, therefore, the temperature of the bath in which the reactor containing the catalyst was immersed must be increased to attempt to maintain the value of the conversion of propylene, as was the case when the content of dopants doubled from $K_{0.05}P_{0.05}$ to $K_{0.1}P_{0.1}$, or an even lower conversion of propylene must be tolerated to maintain the temperature of the bath constant, which is not acceptable on an industrial scale.

It will be appreciated that the value of the yield of acrolein obtained with the catalytic composition of Example 1 according to the invention in a single pass was quite remarkable.

EXAMPLE 5

Preparation of a Control Catalytic Composition

The procedure of Example 1 was repeated, except that 0.285 g of phosphorus pentoxide was introduced into the solution already containing ammonium heptamolybdate and 0.20 g of potassium nitrate into the solution containing the metallic nitrates.

The chemical composition of the active phase thus prepared was therefore $Co_{10}Mo_{12}Fe_1Bi_1K_{0.05}P_{0.1}O_x$ and was not within the ambit of the present invention.

The sequence of operations was identical to that of Example 1. The amount by weight of active phase on the finished catalyst was 18.9%.

EXAMPLE 6

Determination of the Catalytic Activity of the Composition Prepared in Example 5

The catalyst thus prepared was tested in the controlled oxidation of propylene to acrolein under the same conditions as those described in Example 4. The results of the measurements carried out on the catalyst of Example 5 compared to those carried out on the catalyst 1 are reported in Table II below:

EXAMPLE 7

Preparation of a Catalytic Composition According to the Present Invention

The procedure of Example 1 was repeated, except that 0.114 g of 85% phosphoric acid was introduced into the solution already containing ammonium heptamolybdate and 0.20 g of potassium nitrate into the solution containing the metallic nitrates.

The chemical composition of the active phase thus prepared was therefore $Co_{10}Mo_{12}Fe_1Bi_1K_{0.05}P_{0.025}O_x$.

The sequence of operations was identical to that of Example 1. The amount by weight of active phase on the finished catalyst was 19.2%.

EXAMPLE 8

Preparation of a Catalytic Composition According to the Present Invention

This composition differed from that described in Example 7 above by the fact that only 140 g of support were used instead of 210 g.

The sequence of operations was identical to that of Example 7. The amount by weight of active phase on the finished catalyst was 23.9%.

EXAMPLE 9

The procedure of Example 7 was repeated, except that only 105 g of support were used instead of 210 g and 59 g of active phase were used instead of 50 g.

The sequence of operations was identical to that of Example 7. The amount by weight of active phase on the finished catalyst was 33.0%.

EXAMPLE 10

Influence of the Content of Active Phase on the Catalytic Activity

The catalysts thus prepared were tested in the controlled oxidation of propylene to acrolein under the same conditions as those previously described in Example 4, except for the supply of the reagents which was

TABLE II

| Example | Dopants | Amount by weight (%) | Temperature of bath °C. | $X_g$ (%) | $S_{acrolein}$ (%) | $S_{acrylic}$ (%) | $S_{CO-CO_2}$ (%) | $R_{acrolein}$ (%) |
|---|---|---|---|---|---|---|---|---|
| 1 | $K_{0.05}P_{0.05}$ | 19.1 | 351 | 92.2 | 82.5 | 7.6 | 3.7 | 76.0 |
| 1 | $K_{0.05}P_{0.05}$ | 19.1 | 340 | 87.2 | 85.7 | 5.6 | 2.5 | 74.7 |
| 5 | $K_{0.05}P_{0.1}$ | 18.9 | 361 | 85.7 | 84.8 | 6.9 | 2.2 | 72.7 |

It will be seen that the increase in the atomic ratio phosphorus to potassium considerably decreased the catalytic activity. The catalyst of Example 5, even increased to a bath temperature of 361° C., still converted less propylene than the catalyst doped to atomic ratio 1 at a temperature of 340° C.

increased. The charge of propylene was increased from 166 to 250 g/h/liter. The results of the measurements carried out on the catalysts of Examples 8 and 9 compared to those carried out on the catalyst of Example 7 are reported in Table III below:

TABLE III

| Example | Dopants | Amount by weight (%) | Temperature of bath °C. | $X_g$ (%) | $S_{acrolein}$ (%) | $S_{acrylic}$ (%) | $S_{CO-CO_2}$ (%) | $R_{acrolein}$ (%) |
|---|---|---|---|---|---|---|---|---|
| 7 | $K_{0.05} P_{0.025}$ | 19.2 | 400 | 95.8 | 64.7 | 25.9 | 4.6 | 62.0 |
| 8 | $K_{0.05} P_{0.025}$ | 23.9 | 370 | 90.9 | 82.0 | 10.8 | 2.1 | 74.5 |
| 9 | $K_{0.05} P_{0.025}$ | 33.0 | 346 | 95.0 | 79.7 | 11.5 | 2.9 | 76.1 |

It will be seen that the increase in the amount by weight of active phase on the finished catalyst, all other conditions being equal, permitted operating at a lower bath temperature. This also provided perceptibly increased yields of acrolein.

EXAMPLE 11

Influence of the Content of Active Phase on the Mechanical Resistance of the Catalysts The mechanical resistance of the finished catalysts was determined by attrition test as follows:

100 g of finished catalyst were introduced into a Plexiglass® drum of exterior diameter 200 mm and of width 40 mm fixed on the horizontal shaft of a motor revolving at 10 revolutions per minute. In the interior of the drum were fixed, at regular intervals, 6 planar blades of Plexiglass® 45 mm long and 40 mm wide, inclined at 40° with respect to the diameter traversing their fixing base.

The direction of rotation of the drum was such that, if the vector of the tangential velocity of the drum is represented by a point of fixation of any one of the blades, this would provide an angle of 50° with the blade.

The drum was rotated for 5 minutes, then the spheres were removed from the drum and weighed after sieving to separate the fines. The mass thus determined is $m_5$. Dust was removed from the apparatus, then the spheres were reintroduced. A new weighing was carried out at the end of 10 minutes, providing a mass $m_{15}$.

The rate of attrition is defined as the proportion of active phase removed by the attrition device. It is calculated with respect to the amount T of active phase in the following manner:

After 5 minutes, the rate of attrition, in %, had the value $(100-m_5) \times 100/T$.

After a total of 15 minutes attrition, the rate had the value $(100-m_{15}) \times 100/T$.

The measurements of attrition carried out on the catalysts of Examples 7, 8 and 9 increasing in content of active phase, all other conditions being equal, are reported in Table IV below:

TABLE VI

| Example | Dopants | Amount T (%) | Rate of attrition at 5 min (%) | Rate of attrition at 15 min (%) |
|---|---|---|---|---|
| 7 | $K_{0.05} P_{0.025}$ | 19.2 | 0.62 | 1.82 |
| 8 | $P_{0.05} P_{0.025}$ | 23.9 | 1.52 | 5.32 |
| 9 | $K_{0.05} P_{0.025}$ | 33.0 | 3.64 | 12.6 |

It will be seen that, effectively, the increase in the content of active phase resulted in a decrease in mechanical resistance.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A catalyst composition adopted for the oxidation of olefins, which comprises a particulate support substrate uniformly coated with 15% to 33% by weight of an adherent layer of a catalytically active phase, said support substrate comprising inert and solid spheres having a diameter ranging from 0.5 to 6 mm, said catalytically active phase comprising a catalytically effective amount of bismuth and iron molybdate, dopant amounts of phosphorus and potassium and, optionally, at least one other catalytically active metal or non-metal, and said phosphorus and said potassium each being present in said catalytically active phase in an atomic quantity ranging from 0.005 to 0.06 per 12 atoms of molybdenum, or of molybdenum plus any tungsten therein.

2. The catalyst composition as defined by claim 1, said phosphorus and said potassium each being present in said catalytically active phase in an atomic quantity ranging from 0.01 to 0.03 per 12 atoms of molybdenum, or of molybdenum plus any tungsten therein.

3. The catalyst composition as defined by claim 1, said catalytically active phase comprising from 20% to 30% by weight thereof.

4. The catalyst composition as defined by claim 1, wherein the atomic ratio P/K between the phosphorus and potassium in said catalytically active phase ranges from 0.3 to 3.

5. The catalyst composition as defined by claim 4, said ratio P/K ranging from 0.5 to 1.5.

6. The catalyst composition as defined by claim 1, said inert solid spheres comprising said particulate support substrate having a surface roughness ranging from 0.1 to 0.2.

7. The catalyst composition as defined by claim 1 comprising a catalytically active phase having the general formula

$$A_a Mo_b W_c Bi_d Fe_e P_f K_g B_h C_i O_x$$

in which A is an atom of cobalt, nickel, manganese, magnesium and/or lead; B is an atom of arsenic and/or boron; C is an atom of an alkali metal other than potassium and/or an atom of an alkaline earth metal other than magnesium; a is the sum of the numbers of atoms of the elements A and ranges from 2 to 12, with the proviso that when A is cobalt alone, a ranges from 8 to 10; b is a number ranging from 10 to 12; c is a number ranging from 0 to 2 and the sum (b+c) has a value of 12; d is a number ranging from 0.5 to 4; e is a number ranging from 0.5 to 4; f and g are each numbers ranging from 0.005 to 0.06; h is the sum of the numbers of atoms of the elements B and ranges from 0 to 4; i is the sum of the numbers of atoms of the elements C and ranges from 0 to 0.5; x is the number of atoms of oxygen required to satisfy the valencies of the other constituents.

8. The catalyst composition as defined by claim 7, wherein said catalytically active phase, A is an atom of cobalt.

9. The catalyst composition as defined by claim 7, wherein said catalytically active phase, the ratio f/g ranges from 0.3 to 3.

10. The catalyst composition as defined by claim 7, said catalytically active phase comprising the crystallographic phase, $Bi_3Fe_1Mo_2O_{12}$, and having the following X-ray diffraction spectrum:

| d (Å) | Relative visual intensity |
|---|---|
| 3.17 | very large |
| 3.14 | very strong |
| 2.91 | strong |
| 2.69 | weak |
| 2.63 | strong |
| 1.87 | very very weak |

* * * * *